United States Patent [19]

Février et al.

[11] Patent Number: 4,763,009

[45] Date of Patent: Aug. 9, 1988

[54] METHOD AND APPARATUS FOR REMOTELY MEASURING THE DISTRIBUTION OF A PHYSICO-CHEMICAL PARAMETER IN A MEDIUM

[75] Inventors: Hervé Février, Massy; Jean Robieux, Chatenay Malabry; André Tardy, Egly, all of France

[73] Assignee: Compagnie Generale D'Electricite, Paris Cedex, France

[21] Appl. No.: 8,896

[22] Filed: Jan. 30, 1987

[30] Foreign Application Priority Data

Jan. 30, 1986 [FR] France .................... 86 01304

[51] Int. Cl.$^4$ ............................ G01N 21/64
[52] U.S. Cl. .................... 250/458.1; 250/227; 250/459.1
[58] Field of Search .......... 250/227, 461.2, 461.1, 250/459.1, 458.1; 374/161, 131

[56] References Cited

U.S. PATENT DOCUMENTS

| | | | |
|---|---|---|---|
| 4,409,476 | 10/1983 | Löfgren et al. | 250/227 |
| 4,433,238 | 2/1984 | Adolfsson et al. | 250/227 |
| 4,626,693 | 12/1986 | Hirschfeld | 250/458.1 |
| 4,644,154 | 2/1987 | Brogårdh et al. | 250/227 |
| 4,673,299 | 6/1987 | Dakin | 374/131 |

FOREIGN PATENT DOCUMENTS 0050306 10/1981 European Pat. Off.
2484639 12/1981 France.
2156513 10/1985 United Kingdom.

OTHER PUBLICATIONS

R. L. McKenzie and K. P. Gross, "Two-Photon Excitation of Nitric Oxide Fluorescence as a Temperature Indicator in Unsteady Gasdynamic Processes", Applied Optics, vol. 20, No. 12, (Jun. 15, 1981), pp. 2153-2165.

S. A. Kingsley, "Distributed Fiber-Optic Sensors", Advances in Instrumentation, vol. 39, (Oct. 22-25, 1984), pp. 315-380, Research Triangle Park, NC.

"Remote Measurement of Temperature Distribution Using an Optical Fiber", A. G. Hartog et al., Conference Europeenee Sur Les Communications Optiques, (Sep. 19, 1982), pp. 215-220.

Primary Examiner—Janice A. Howell
Assistant Examiner—Constantine Hannaher
Attorney, Agent, or Firm—Sughrue, Mion, Zinn, Macpeak, and Seas

[57] ABSTRACT

The invention relates to a method and to apparatus for remotely measuring the distribution of a physico-chemical parameter in a medium. The method consists in exciting measurement points (20) situated in a medium (17) in succession via an optical fiber (18), with each point (20) being excited by two light pulses of different wavelengths offset from each other in time occurring simultaneously at said point, each measurement point returning radiation at a third wavelength representative of the temperature of the measurement point. The apparatus includes two lasers (3, 4) emitting different wavelengths, a delay circuit (5) for delaying the light pulse from one (4) of the two lasers, and the measurement points include a material sensitive to biphotonic excitation.

8 Claims, 3 Drawing Sheets

METHOD AND APPARATUS FOR REMOTELY MEASURING THE DISTRIBUTION OF A PHYSICO-CHEMICAL PARAMETER IN A MEDIUM

FIELD OF THE INVENTION

The present invention relates to a method and an apparatus for remotely measuring the distribution of a physico-chemical parameter in a medium. The method is of the type comprising:

light pulse excitation of measurement points situated in said medium and subjected to the physico-chemical parameter, said excitation being emitted from a station at a distance from said medium and being transmitted to the measurement points by an optical waveguide, each excited measurement point returning optical radiation towards the station along the waveguide, said return optical radiation being representative of the value of the physical parameter at said measurement point; and processing the returned optical radiation in the station;

The physical parameters may, for example, be temperature or pressure or the chemical composition of the medium.

BACKGROUND OF THE INVENTION

A device of this type is described in an article entitled "Mesure à distance de la distribution de température à l'aide d'une fibre optique" (Remotely measuring temperature distribution using an optical fiber) by Hartog et al taken from "European Conference on Optical Communications" (E.C.O.C.), Cannes 1983, session A IV—Propiétés des fibres (III) (Fiber properties III), pages 215 to 220. With this device, proposals are made to measure the temperature at measurement points which are distributed along a liquid-core optical fiber. Excitation pulses are provided by a laser and the returned optical radiation is constituted by optical signals backscattered from the measurement points. The returned optical radiation is processed by measuring the level of said signals which level is a function of the temperature at the measurement points. The time taken by the signals to reach the station depends directly on the speed of propagation of optical radiation in the fiber: the time taken is therefore representative of the positions of the measurement points along the fiber. A curve can then be plotted as a function of time showing variations in the level of the backscattered optical signals as received by the station. After taking account of diffusion in the fiber, the temperature of the measurement points can readily be deduced as a function of their positions along the fiber.

In this apparatus, the emission of backscattered optical signals coincides in time with the instants at which the measurement points are excited. However, it is obvious that the method described in the article cannot be used when the characteristic of the backscattered optical radiation which is to be measured has a duration which is long relative to the propagation time of optical radiation in the fiber. By way of example, an optical fiber apparatus of this type in which the characteristic to be measured in the return radiation is the lifetime of fluorescence in a rare earth dopant of the fiber core cannot be made in practice since the lifetime in question is about 500 microseconds, which corresponds to a path length of 100 km along the optical fiber. In this case, the spectroscopical information returning from various measurement points would be superposed in time on reception by the processing circuit, and such information would therefore be unusable since it would be impossible to localize any of the measurement points.

SUMMARY OF THE INVENTION

The aim of the present invention is to make use of the relatively slow-varying spectroscopical properties of a material in order to provide apparatus for remotely measuring the distribution of a physico-chemical parameter in a medium, said apparatus providing good spatial resolution.

The present invention provides a method for remotely measuring the distribution of a physico-chemical parameter in a medium, the method being of the above-mentioned type and being characterized in that said optical excitation comprises respective special excitations for the various measurement points performed one after the other, the excitation of a measurement point being performed by emitting in succession from the station a first pulse having a first optical wavelength and a second pulse having a second optical wavelength different from the first wavelength, the time interval between said two pulses being chosen so that the second pulse encounters the first pulse along the waveguide at said measurement point, the optical excitation of said measurement point being created by said point being illuminated simultaneously by said first and second pulses at the instant when said pulses encounter each other, the return optical radiation delivered by the measurement point towards the station in response to said optical excitation including at least one third wavelength different from the first and second wavelengths.

The present invention also provides apparatus for remotely measuring the distribution of a physico-chemical parameter in a medium, said apparatus being subjected to the physico-chemical parameter and comprising measurement points, the apparatus comprising:

a station at a distance from said medium, said station including means for emitting light pulses;

an optical waveguide disposed to connect the station to the measurement points, one end of said waveguide situated in the station being connected to the outlet from emission means for transmitting light pulses along the waveguide to the measurement points in order to excite said measurement points, and each point responding by delivering return optical radiation propagating in the opposite direction along the waveguide towards the station;

a photoelectric receiver disposed in the station and optically connected to said end of the waveguide in order to receive the returned optical radiation; and a processor circuit connected to the electrical outlet of the receiver in order to analyze the returned optical radiation;

said apparatus being characterized in that:

said light pulse emission means comprise:
 a first light generator capable of emitting a first light pulse at a first optical wavelength;
 a second light generator capable of emitting a second light pulse at a second optical wavelength, the outlets from said first and second light generators being connected to said end of the waveguide;
 a control circuit capable of emitting an electrical start pulse for scanning each measurement point, the outlet from said circuit being connected to the inlet of the first light generator and to the processor circuit; and a delay circuit having its input connected to the output from the control circuit and having its output connected to the inlet to the second light generator, said circuit being capable of delaying the electrical start pulse by a predetermined time interval so that the second pulse encounters the first pulse along the waveguide at the measurement point being scanned;

said measurement points including a material suitable for delivering optical return radiation at a third wavelength different from said first and second wavelengths at the moment that said first and second pulses encounter each other; and said apparatus further including an optical filter disposed in the station between said end of the waveguide and the photoelectric receiver, said filter passing only the return optical radiation having said third wavelength.

In a first embodiment of apparatus in accordance with the invention, the waveguide comprises an optical fiber situated in said medium, with the material of the measurement points being constituted by the core of the optical fiber.

In a first version of said first embodiment, the waveguide comprises means for connecting one end of the optical fiber to the station, with the other end of the fiber being free, and with the encounter between the first and second pulses taking place after the first pulse has been reflected from the free end of the optical fiber.

In a second version of the first embodiment, the waveguide comprises means for connecting both ends of the optical fiber to the station, with the output from the first light generator being coupled to a first end of the optical fiber, the output from the second light generator being coupled to the second end of the optical fiber, and the optical filter being coupled to the second end of the optical fiber.

In a second embodiment of the apparatus in accordance with the invention, the measurement points comprise interaction cells distributed discontinuously in said medium, said medium being fluid, the walls of said cells being permeable to said fluid medium, and the material at the measurement points being contained in said cells and being transparent to radiation at said first, second, and third wavelengths.

In a first version of the second embodiment, the waveguide comprises fragments of optical fiber disposed end-to-end in series, with the interaction cells being interspersed between said fragments, and with the first and second pulses encountering each other after said first pulse has been reflected from the other end of the waveguide.

In a second version of this second embodiment, the waveguide comprises a main optical fiber situated in said medium outside the interaction cells, with branch optical fibers being connected on said main optical fiber and terminating at respective different interaction cells, and with terminal fragments of optical fibers of mutually different lengths being connected to respective different interaction cells, and each terminating in an extreme face, with the first pulse encountering the second pulse in an interaction cell after the first pulse has been reflected on the extreme face of the terminal fragment connected to said cell.

BRIEF DESCRIPTION OF THE DRAWINGS

The particular forms whereby the subject matter of the present invention is implemented are described below by way of example with reference to the accompanying drawings, in which.

DESCRIPTION OF THE PREFERRED EMBODIMENTS

Figure 1:
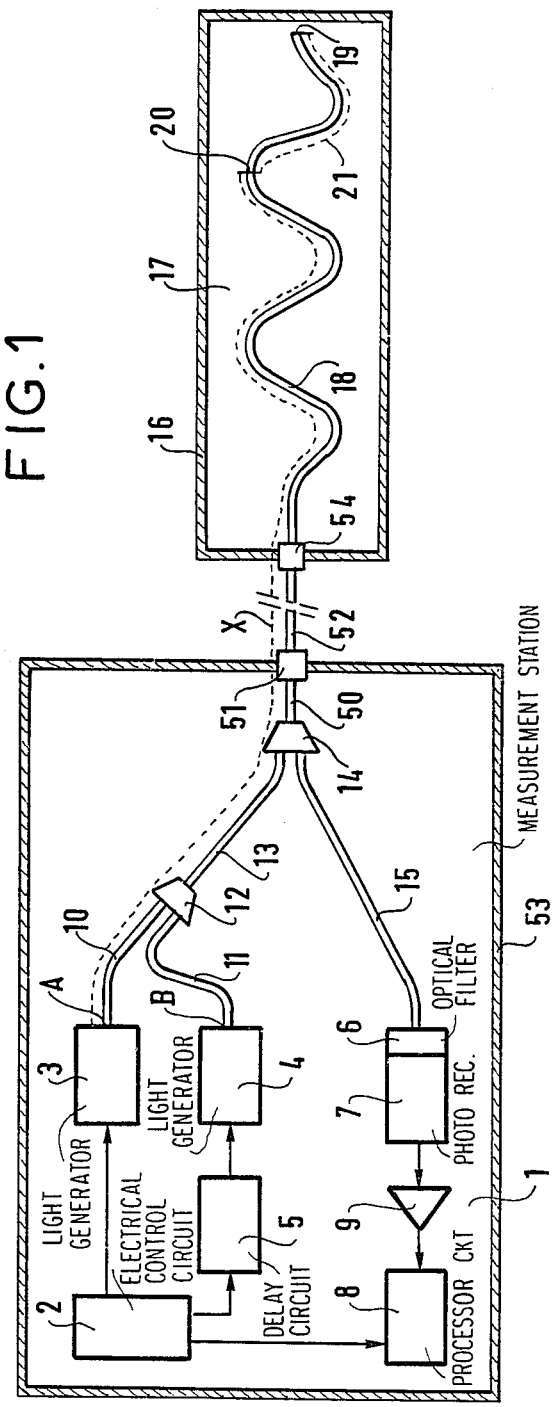
FIG. 1 is a diagram of a first variant of apparatus in accordance with the invention, and including a first type of sensor.

In FIG. 1, a measurement station 1 comprises an electrical control circuit 2 whose output is connected to the electrical input of a first light generator 3. Another output from the circuit 2 is connected to the electrical input of a second light generator 4 via a delay circuit 5. Preferably, the light generators 3 and 4 are laser generators. The station 1 also includes an optical filter 6 disposed in front of the photosensitive surface of a photoelectric receiver 7 whose electrical output is connected to a processor circuit 8 via an amplifier 9. Another output from the control circuit 2 is connected to the processor circuit 8.

One end of an optical fiber 10 is coupled to the output from the light generator 3, while one end of an optical fiber 11 is coupled to the output from the light generator 4. The free ends of the fibers 10 and 11 are connected to respective ones of two parallel branches of an optical Y-coupler 12 which connects said parallel-connected branches to a collector branch. An optical fiber 13 connects the collector branch of the coupler 12 to a parallel-connected branch of another optical Y-coupler 14. An optical fiber 15 connects the other parallel branch of the coupler 14 to the inlet of the optical filter 6. The common branch of the coupler 14 is connected via a length of optical fiber 50 and a two-branch coupler 51 to one end of an optical fiber 52 which provides an optical connection between the measurement station 1 and an enclosure 16 containing a medium 17 such as air. The coupler 51 is inserted through a wall 53 of the measurement station 1, said wall 53 enclosing the elements 2 to 14 and 50. The other end of the optical fiber 52 is connected via a two-branch coupler 54 to one end of an optical fiber 18 which is disposed inside the enclosure 16, with the coupler 54 passing through the wall of the enclosure 16.

The apparatus shown in FIG. 1 operates as follows.

The spatial distribution along the fiber 18 of temperature in the medium 17 is to be measured.

The control circuit 2 emits an electrical starting pulse which causes the laser 3 to emit a first light pulse of very short duration and of wavelength L1. The starting electrical pulse emitted by the circuit 2 is delayed by the circuit 5 for a time interval t so that the laser 4 emits a second very short light pulse, of wavelength L2 which is delayed by the time interval t relative to the first pulse. The first pulse propagates successively along fibers 10, 13, 50, 52, and 18. It is returned in the opposite direction by a reflection on the outlet face 19 of the fiber 18. If necessary, this face 19 may be provided with a reflective coating. The second pulse propagates successively along fibers 11, 13, 50, 52, and 18 and encounters the first pulse as returned from the face 19 at a point 20 along the fiber 18. The point 20 is situated at a distance 21 from the face 19, with said distance being measured along the fiber 18. The distance 21 depends on the speed of pulse propagation along the fiber 18 and its value is directly dependent on the time interval t between the first and second pulses.

The core of the optical fiber 18 is made of a glass which is doped using a rare earth. When this glass is simultaneously illuminated by radiation of wavelength L1 from the first pulse and by radiation of wavelength L2 from the second pulse, its atoms are subjected to biphotonic absorption, which raises their quantum level from an initial non-excitation level (e.g. base level) to an excited level. A de-excitation phenomenon takes place spontaneously from said excited level, thereby producing light emission at wavelength L3. This light emission or luminescence is emitted from point 20 which is the only point of the optical fiber core to be illuminated simultaneously by both light pulses of wavelengths L1 and L2. The lifetime of this luminescence is representative of the temperature of point 20 on the fiber 18, i.e. of the temperature of the medium immediately surrounding said point 20. This luminescence propagates along the fibers 18, 52, 50, and 15, and passes without absorption through the filter 6 which allows radiation to pass only at wavelength L3. The photodetector 7 transforms the luminescence into an electrical pulse which is amplified by the amplifier 9. The lifetime of the luminescence signal is then measured by the circuit 8. This lifetime represents the temperature of the medium at point 20. The position of the point 20 on the fiber is easily determined from the delay t between the first and second light pulses.

The distance measured along the optical fibers between the emission points (A or B) of the two light pulses and the point 20 along the fiber 18 is given by:

$$x = L - (vt)/2$$

where L is the distance along the optical fibers between the points A or B and the end point 19 of the fiber 18, and v is the speed of propagation of optical radiation at wavelengths L1 and L2 along the optical fibers and ignoring the duration of said excitation light pulses.

The above-described operations can be used to measure the temperature of the medium 17 at a point 20 which is determined by its position along the fiber 18. In order to measure the temperature at another point along the fiber, the same operations are repeated except that the value of the time interval t between the two pulses emitted respectively by the generators 3 and 4 is modified. It can thus be seen that it is possible to measure the continuous temperature distribution of the medium along the fiber 18 which acts as a temperature-measuring sensor.

Figure 2:
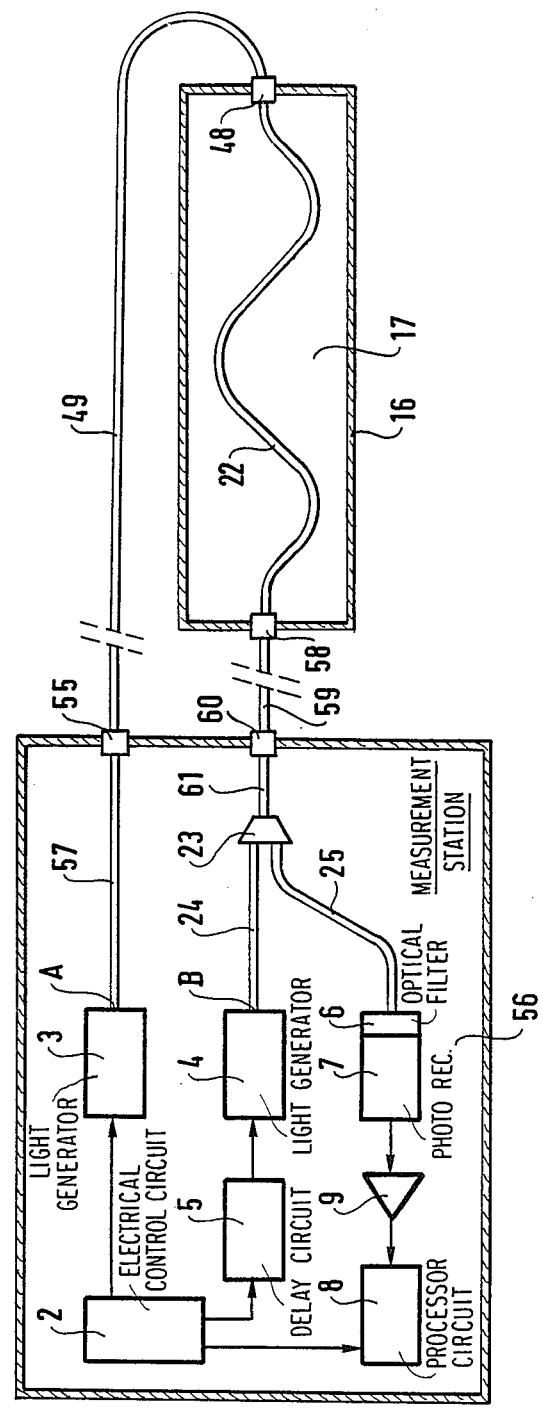
FIG. 2 is a diagram of a second variant of apparatus in accordance with the invention and including a second type of sensor.

FIG. 2 shows a second variant of apparatus in accordance with the invention, said variant including elements which are identical to those of the apparatus shown in FIG. 1, with said identical elements being designated by the same references. The FIG. 2 apparatus differs from the FIG. 1 apparatus in that the two ends of the optical measurement fiber 22 are optically connected respectively to the generator 3 and to the generator 4. The connection with the generator 3 is made via a two-branch optical coupler 48 inserted through the wall of the enclosure 16, and an optical fiber 49, and a two-branch optical coupler 55 inserted through the wall of the measurement station 56, followed by an optical fiber 57. The connection with the generator 4 takes place through a two-branch coupler 58 inserted through the wall of the enclosure 16, via an optical fiber 59, via a two-branch coupler 60 inserted through the wall of the station 56, via an optical fiber 61, via a Y-coupler 23, and via an optical fiber 24 which is connected to one of the parallel branches of the coupler 23. Another optical fiber 25 connects the other parallel connected branch of the coupler 23 to the inlet to the filter 6.

The operation of the apparatus shown in FIG. 2 differs from that of the apparatus shown in FIG. 1 by virtue of the fact that the first light pulse emitted by the generator 3 directly encounters the second light pulse emitted by the generator 4, since these two pulses propagate in opposite directions along the fiber 22. The first pulse is thus not subjected to reflection prior to encountering the second pulse. Naturally the delay period t is chosen so that the point where the two pulses encounter each other is situated along the measurement optical fiber 22. When the physical parameter to be measured is temperature, the optical fiber 22 may be of a type analogous to that of the optical fiber 18 shown in FIG. 1.

For example, when measuring temperature, the generators 3 and 4 in the apparatuses shown in FIGS. 1 and 2 may be laser emitters having respective emission wavelengths L1 and L2 lying in the range 1 to 1.4 micrometers. The core material of the fibers 18 and 22 acting as sensors may be neodymium-doped glass. Under these conditions, the luminescence wavelength L3 is about 1.06 micrometers. It is observed that an increase in the temperature to be measured corresponds to a reduction in the lifetime of the luminescence.

The apparatuses shown in FIGS. 1 and 2 can also be used for measuring the pressure in the medium contained in the enclosure. The pressure exerted at a measurement point along the cladding of the fiber 18 or 20 is elastically transmitted from the cladding to the core of the fiber. Under the conditions specified in the paragraph above, it is observed that an increase in pressure corresponds to an increase in the lifetime of the luminescence.

Figure 3:
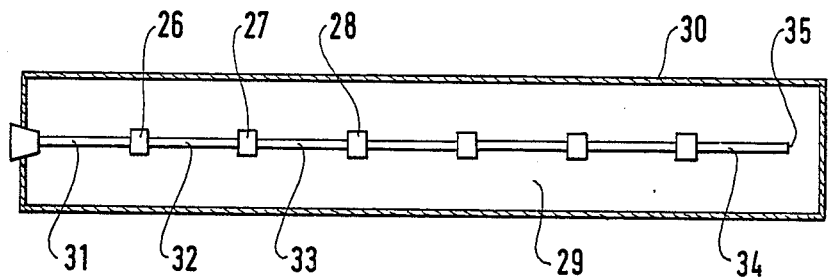
FIGS. 3 and 4 are diagrams of two other types of sensor capable of replacing the sensor shown in FIG. 1, thereby respectively forming third and fourth variants of apparatus in accordance with the invention.

FIG. 3 shows a measurement sensor which may be used instead of the optical fiber 18 in the apparatus shown in FIG. 1. This sensor comprises interaction cells such as 26, 27, and 24 which are discontinuously distributed within the enclosure 30 containing a medium 29 such as a gas whose chemical composition is to be measured, for example. These cells are interspersed between fragments of optical fiber such as 31, 32, and 33 disposed end-to-end in series.

Each cell is delimited by a wall which is permeable to the medium 29 and contains a material capable of chemically reacting with the component parts of said fluid medium, said material being transparent to the emitted optical radiation at wavelengths L1 and L2, and to the returned optical radiation.

The interaction cells constitute the measurement points of the apparatus, and the fragments of optical fiber do not contain reactive material and serve solely for transmitting optical radiation.

When the material contained in these cells is subjected to simultaneous biphotonic excitation at wavelengths L1 and L2, it emits return optical radiation whose characteristics are representative of the chemical composition of the fluid medium 29. In this case, the return radiation may, for example, include several wavelengths, each specific to a chemical element in the fluid medium to be analyzed. The processor circuit 8 (FIG. 1) may thus include means for measuring these return wavelengths. As in the FIG. 1 case, the excitation radiation of wavelength L1 is reflected from the end face 35 of the terminal fragment 34 prior to encountering the excitation radiation of wavelength L2 in an interaction cell.

Figure 4:
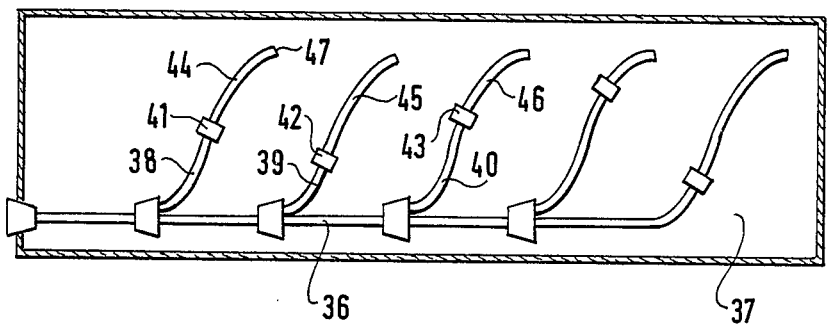

FIG. 4 shows another type of measurement sensor, which is also capable of replacing the optical fiber 18 in the apparatus shown in FIG. 1. This sensor comprises a main optical fiber 36 disposed in a fluid medium 37, with branch optical fibers such as 38, 39, and 40 being connected to the main fiber 36 and respectively leading to interaction cells 41, 42, and 43, each of which has a corresponding terminal optical fibers 44, 45, and 46 connected thereto. The operation of the apparatus using this type of sensor is analogous to that of the apparatus using the sensor shown in FIG. 3. Each second pulse encounters the corresponding first pulse in an interaction cell 41 after the first pulse has been reflected from the end face 47 of the terminal fiber 44 connected to said cell.

Naturally, the terminal optical fibers 44, 45, and 46 should be of mutually different lengths, since these lengths correspond to different delays between the two excitation pulses.

Clearly the different variants of apparatus in accordance with the invention as described above can be used to concentrate the optical excitation of the active medium at a single measurement point. The return signals from the various measurement points may be superposed on reception since measurements relating to different measurement points are performed separately one after the other.

We claim:

1. A method of remotely measuring the distribution of a physico-chemical parameter in a medium, the method comprising:

light pulse excitation of measurement points situated in said medium and subjected to the physico-chemical parameter, said excitation being emitted from a station at a distance from said medium and being transmitted to the measurement points by an optical waveguide, each excited measurement point returning optical radiation towards the station along the waveguide, said return optical radiation being representative of the value of the physical parameter at said measurement point; and processing the returned optical radiation in the station;

the method being characterized in that said optical excitation comprises respective special excitations for the various measurement points performed one after the other, the excitation of a measurement point being performed by emitting in succession from the station a first pulse having a first optical wavelength and a second pulse having a second optical wavelength different from the first wavelength, the time interval between said two pulses being chosen so that the second pulse encounters the first pulse along the waveguide at said measurement point, the optical excitation of said measurement point being created by said point being illuminated simultaneously by said first and second pulses at the instant when said pulses encounter each other, the return optical radiation delivered by the measurement point towards the station in response to said optical excitation including at least one third wavelength different from the first and second wavelengths.

2. Apparatus for remotely measuring the distribution of a physico-chemical parameter in a medium, said apparatus being subjected to the physico-chemical parameter and comprising measurement points, the apparatus comprising:

a station at a distance from said medium, said station including means for emitting light pulses;

an optical waveguide disposed to connect the station to the measurement points, one end of said waveguide situated in the station being connected to the outlet from emission means for transmitting light pulses along the waveguide to the measurement points in order to excite said measurement points, and each point responding by delivering return optical radiation propagating in the opposite direction along the waveguide towards the station;

a photoelectric receiver disposed in the station and optically connected to said end of the waveguide in order to receive the returned optical radiation; and a processor circuit connected to the electrical outlet of the receiver in order to analyze the returned optical radiation;

said apparatus being characterized in that:

said light pulse emission means comprise:

a first light generator capable of emitting a first light pulse at a first optical wavelength;

a second light generator capable of emitting a second light pulse at a second optical wavelength, the outlets from said first and second light generators being connected to said end of the waveguide;

a control circuit capable of emitting an electrical start pulse for scanning each measurement point, the outlet from said curcuit being connected to the inlet of the first light generator and to the processor circuit; and a delay circuit having its input connected to the output from the control circuit and having its output connected to the inlet to the second light generator, said circuit being capable of delaying the electrical start pulse by a predetermined time interval so that the second pulse encounters the first pulse along the waveguide at the measurement point being scanned;

said measurement points including a material suitable for delivering optical return radiation at a third wavelength different from said first and second wavelengths at the moment that said first and second pulses encounter each other; and said apparatus further including an optical filter disposed in the station between said end of the waveguide and the photoelectric receiver, said filter passing only the return optical radiation having said third wavelength.

3. Apparatus according to claim 2, characterized in that the waveguide comprises an optical fiber situated in said medium, the material of the measurement points being constituted by the core of the optical fiber.

4. Apparatus according to claim 3, characterized in that the waveguide comprises means for connecting one end of the optical fiber to the station, with the other end of the optical fiber being free, and with the first and second pulses encountering each other after the first pulse has been reflected from the free end of the optical fiber.

5. Apparatus according to claim 3, characterized in that the waveguide includes means for connecting both ends of the optical fiber to the station, with the outlet from the first light generator being coupled to a first end of the optical fiber, with the outlet from the second light generator being coupled to the second end of the optical fiber, and with the optical filter being coupled to the second end of the optical fiber.

6. Apparatus according to claim 2, characterized in that the measurement points include interaction cells distributed discontinuously in said medium, said medium being fluid, the walls of said cells being permeable to said fluid medium, the material of the measurement points being contained in said cell and being transparent to radiation at said first, second, and third wavelengths.

7. Apparatus according to claim 6, characterized in that the waveguide comprises optical fiber fragments disposed end-to-end in series, with the interaction cells interspersed between said fragments, and with the encounter between the second and first pulses taking place after said first pulse has been reflected from the other end of the waveguide.

8. Apparatus according to claim 6, characterized in that the waveguide comprises a main optical fiber situated in said medium outside said interaction cells, with branch optical fibers being connected to said main optical fiber and leading to respective different interaction cells, and with terminal optical fiber fragments of mutually different lengths being connected to respective different interaction cells and each terminating in an extreme face, with the first pulse encountering the second pulse in an interaction cell after the first pulse has been reflected from the extreme face of the terminal fragment (44) connected to said cell.

* * * * *